United States Patent [19]

Simes et al.

[11] 4,163,911
[45] Aug. 7, 1979

[54] PERMANENT MAGNET TRANSLATIONAL MOTOR FOR RESPIRATORS

[75] Inventors: James G. Simes; Donald H. Gillott, both of Sacramento, Calif.

[73] Assignee: Sutter Hospitals Medical Research Foundation, Sacramento, Calif.

[21] Appl. No.: 760,556

[22] Filed: Jan. 19, 1977

Related U.S. Application Data

[63] Continuation of Ser. No. 544,650, Jan. 27, 1975, abandoned, which is a continuation-in-part of Ser. No. 323,501, Jan. 15, 1973, Pat. No. 3,863,082.

[51] Int. Cl.² .................................................. H02K 33/18
[52] U.S. Cl. ...................................... 310/27; 417/417; 128/145.6
[58] Field of Search ....................... 310/27, 117–119; 128/145.5, 145.8, 145.6

[56] References Cited

U.S. PATENT DOCUMENTS

| | | | |
|---|---|---|---|
| 1,996,160 | 4/1935 | König | 417/416 |
| 2,931,925 | 4/1960 | Dölz | 310/27 |
| 3,384,021 | 5/1968 | Perron | 417/417 |
| 3,500,079 | 3/1970 | Barthalon | 310/27 X |
| 3,619,673 | 11/1971 | Helms | 310/13 |
| 3,743,870 | 7/1973 | Hunt | 310/13 |
| 3,863,082 | 1/1975 | Gillott et al. | 310/27 |

Primary Examiner—Donovan F. Duggan
Attorney, Agent, or Firm—Christie, Parker & Hale

[57] ABSTRACT

A permanent magnet translational motor includes a double-ended cylindrical outer shell having a hollow interior, a solid cylindrical core in the hollow interior coaxially aligned with the longitudinal axis of the shell, and permanent magnet segments secured to the interior surface of the shell and surrounding the core. The permanent magnets develop a radial magnetic field across the air gap between the magnets and the core. A moving drive coil mounted on the core slides longitudinally back and forth in the magnetic field in response to changes in electric current passing through the coil. Opposed mounting brackets on the moving drive coil extend outwardly through longitudinally extending slotted openings in opposite sides of the shell for connection to a respirator piston. The drive coil is driven back and forth in response to an adjustable D.C. voltage waveform to control the pressure build up in the patient's lungs with respect to time during each inspiratory cycle of the respirator.

13 Claims, 5 Drawing Figures

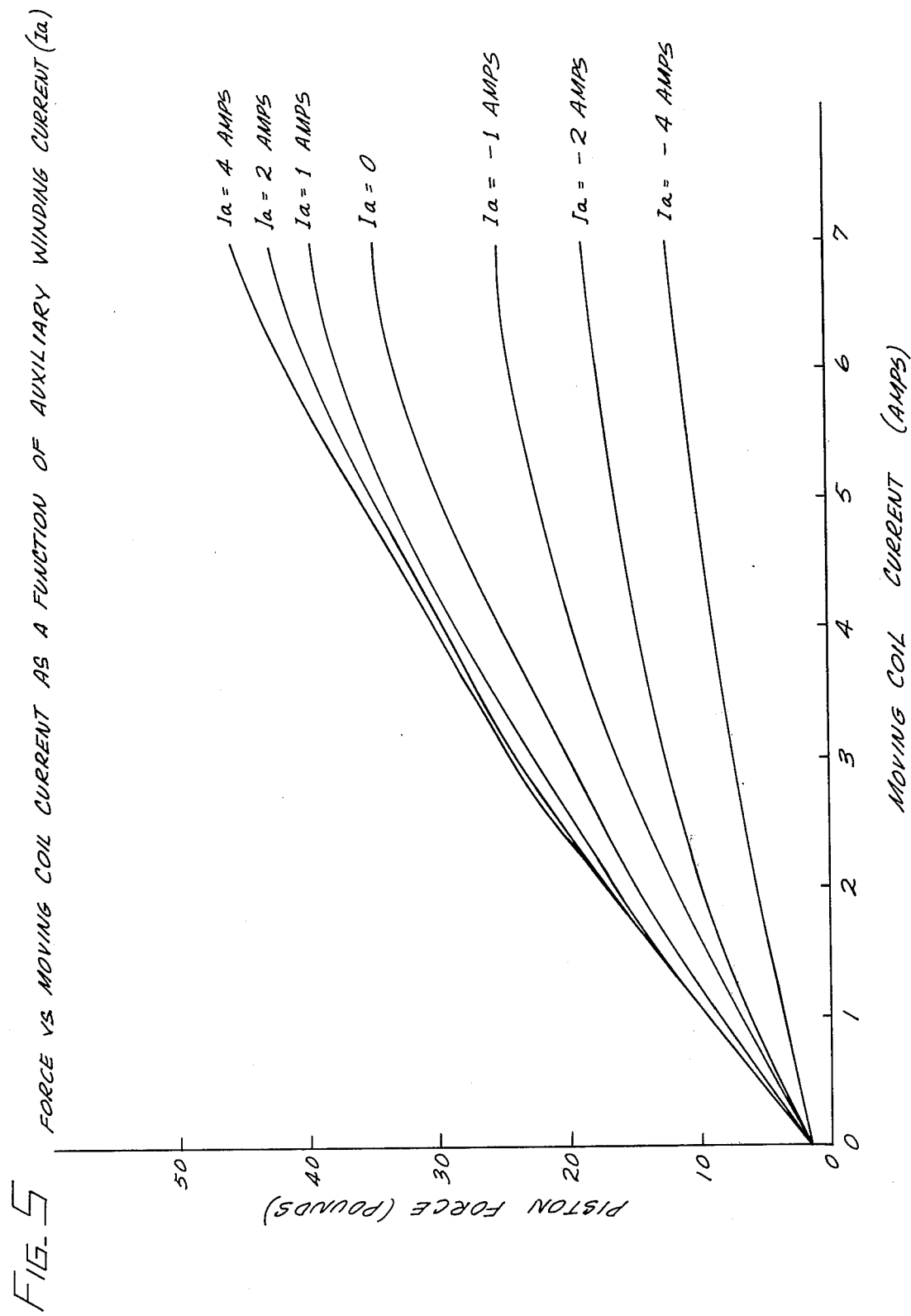

PERMANENT MAGNET TRANSLATIONAL MOTOR FOR RESPIRATORS

CROSS-REFERENCE TO RELATED APPLICATIONS

This is a continuation of application Ser. No. 544,650, filed Jan. 27, 1975, now abandoned which, in turn, is a continuation-in-part of application Ser. No. 323,501, filed Jan. 15, 1973, now U.S. Pat. No. 3,863,082.

BACKGROUND OF THE INVENTION

This invention relates to an improved permanent magnet motor, and also to an improved air delivery system for respirators in which a permanent magnet translational motor provides the linear drive for the respirator piston.

In the past, permanent magnet motors generally have been used in servo systems to apply translational motion to objects whose linear position is to be controlled. A permanent magnet motor generally includes a moving coil mounted on a core of ferromagnetic material which, in turn, is placed in a magnetic field produced by a permanent magnet. Electric current passing through the coil interacts with the magnetic field of the permanent magnet to produce a translational force on the coil parallel to the longitudinal axis of the core to move the coil, and a load attached to the coil, along a linear path. Periodic reversal of the current in the coil moves the coil in a reciprocating fashion to apply reciprocating longitudinal movement to the load.

One typical use of a permanent magnet translational motor is for driving a pen in a strip chart recorder. Such a motor is used in the strip chart recorder Models 7143A and 7143B manufactured by Hewlett Packard Corporation. This permanent magnet motor has a movable coil with a relatively wide air gap between the core and the permanent magnet. Because of the relatively wide air gap, a magnetic flux of relatively low intensity is produced across the gap. This develops a relatively small motor output force of about one pound. The pen drive motor also has a stroke length of about five to ten inches. A stroke of such length is attained because the magnetic field intensity and the current developed in the moving coil are both of such low magnitude that the coil can be moved axially through the five to ten inch stroke without the core being driven into saturation. Because the motor generates a small force, the moving coil may be coupled to the pen unsymmetrically.

Other permanent magnet translational motors have been designed for applications requiring a relatively large output force, say about 30 to 40 pounds. A typical motor used in such applications is the Model 14 computer memory head positioning motor manufactured by Information Magnetics Corporation. This motor includes a ferromagnetic housing with one open end, and a sliding coil mounted on a relatively short, cylindrical steel core inside the housing. The coil moves back and forth in a narrow air gap, which enables a relatively large flux to be developed across the gap. The current passing through the coil interacts with the large flux to produce an output force of about forty pounds at a stroke length of about two inches. The motor is not suitable for use in applications requiring a long stroke length in the neighborhood of about five to ten inches, because the relatively large field over the longer length drives the core into saturation, for motors with stroke lengths of more than two inches, unless a larger cross-sectional area of iron is used.

SUMMARY OF THE INVENTION

This invention provides a permanent magnet translational motor which produces a relatively large output force, say more than forty pounds, through a relatively long stroke length in the neighborhood of about five to ten inches. A typical use for such a motor is for driving the piston of a respirator, where the combination of a relatively large force and long stroke length is necessary to force a given volume of air into the lungs of a patient under a predetermined pressure, volume, and/or flow. The respirator also includes electronic controls for adjusting the output force of the motor so the pressure, volume, and/or flow of the air supplied to each patient can be easily and accurately adjusted.

Briefly, the motor includes a shell with a pair of closed ends enclosing a hollow interior, and an elongated core extending through the hollow interior from one end of the shell to the other. A permanent magnet disposed in the interior of the shell surrounds a predetermined length of the core. The permanent magnet is spaced from the core to form a narrow working air gap between the magnet and the core so that a magnetic field is established radially across the air gap. A movable coil surrounding the portion of the core located in the air gap is supported on the core to slide longitudinally back and forth relative to the core in the magnetic field in response to changes in electric current passing through the coil. The coil has opposed mounting means extending outwardly from it through corresponding openings in the shell for attachment to a load such as a respirator piston. Reciprocating translational motion of the coil through the field is transferred to the load.

In a preferred form of the invention, an auxiliary coil is disposed at one end of the shell. The magnetomotive force generated by the auxiliary coil may either aid or oppose the magnetomotive force of the moving coil, thereby altering the air gap flux for large values of movable coil currents. By proper choice of auxiliary coil current, the maximum available force may be varied without affecting the small current characteristics of the movable coil.

The motor develops a magnetic field of relatively high intensity because (1) the permanent magnet has a relatively high magnetic flux retentivity; (2) the working air gap between the surface of the core and the permanent magnet is relatively narrow, so that the flux developed by the permanent magnet traverses the air gap but not the leakage path, and therefore is not readily dissipated; (3) the core is relatively large size so that it can support the magnetic flux; and (4) the shell is closed at both ends, which reduces by one-half the magnetic flux which would exist in the magnetic parts of a motor with one end open. The coil has a relatively high current-carrying capacity, and the relatively high current interacts with the high intensity magnetic field to generate a relatively large output force in excess of more than about forty pounds.

The auxiliary coil varies the magnetic saturation in the core, and therefore overcomes the tendency of the core to become saturated when the moving coil carries large current as it moves through the magnetic field. This increases the force produced by the movable coil for a given stroke length. Thus, the auxiliary coil can be coupled to an electronic control circuit which, in turn, can be used to adjust the maximum force applied by the coil. This means of adjustment can be important in applications such as respirators, where the pressure, volume, and/or flow developed by the moving respirator piston should be adjustable to meet the needs of various patients.

The use of the permanent magnet motor of this invention in combination with a respirator provides several advantages over prior art respirators. For example, the piston in prior art respirators generally is driven by a rotary drive motor which requires gear reduction, together with relatively complicated mechanical linkages, such as a rack, pinion, joints, and the like, to convert the high frequency rotary motion of the motor into the relatively low frequency translational motion of the piston. On the other hand, the permanent magnet translational motor of this invention provides a respirator drive having no moving parts other than the moving coil assembly of the motor and the piston. This assures extreme mechanical simplicity, reliability and accurate control when compared with prior art respirators. Further, the translational motor of this invention provides a simple means for controlling movement of the respirator piston to deliver a controlled, time-related volume of gas to a patient throughout each inspiratory cycle. The moving drive coil is controlled by an adjustable time-dependent volume waveform which provides the capability of controlling pressure build up in the patient's lungs during each inspiratory cycle. To obtain similar control over the volume waveform in a respirator driven by a rotary motor would require a complicated gear mechanism because of the difficulty in providing adjustments in the approximately sinusoidal motion of the piston driven by a rotary motor and its associated connecting rod and crankshaft.

The permanent magnet translational motor also provides essentially noise-free operation, which is a substantial improvement over prior art respirators which operate at a constant noise level and therefore can be uncomfortable for the patient and the hospital attendants.

BRIEF DESCRIPTION OF THE DRAWINGS

These and other aspects of the invention will be more fully understood by referring to the following detailed description and the accompanying drawings in which:

FIG. 5 is a graph showing the relationship between the force produced by the motor and the current in the moving coil of the motor as a function of the current in the motor's auxiliary coil.

DETAILED DESCRIPTION OF THE PREFERRED EMBODIMENT

Figure 1:
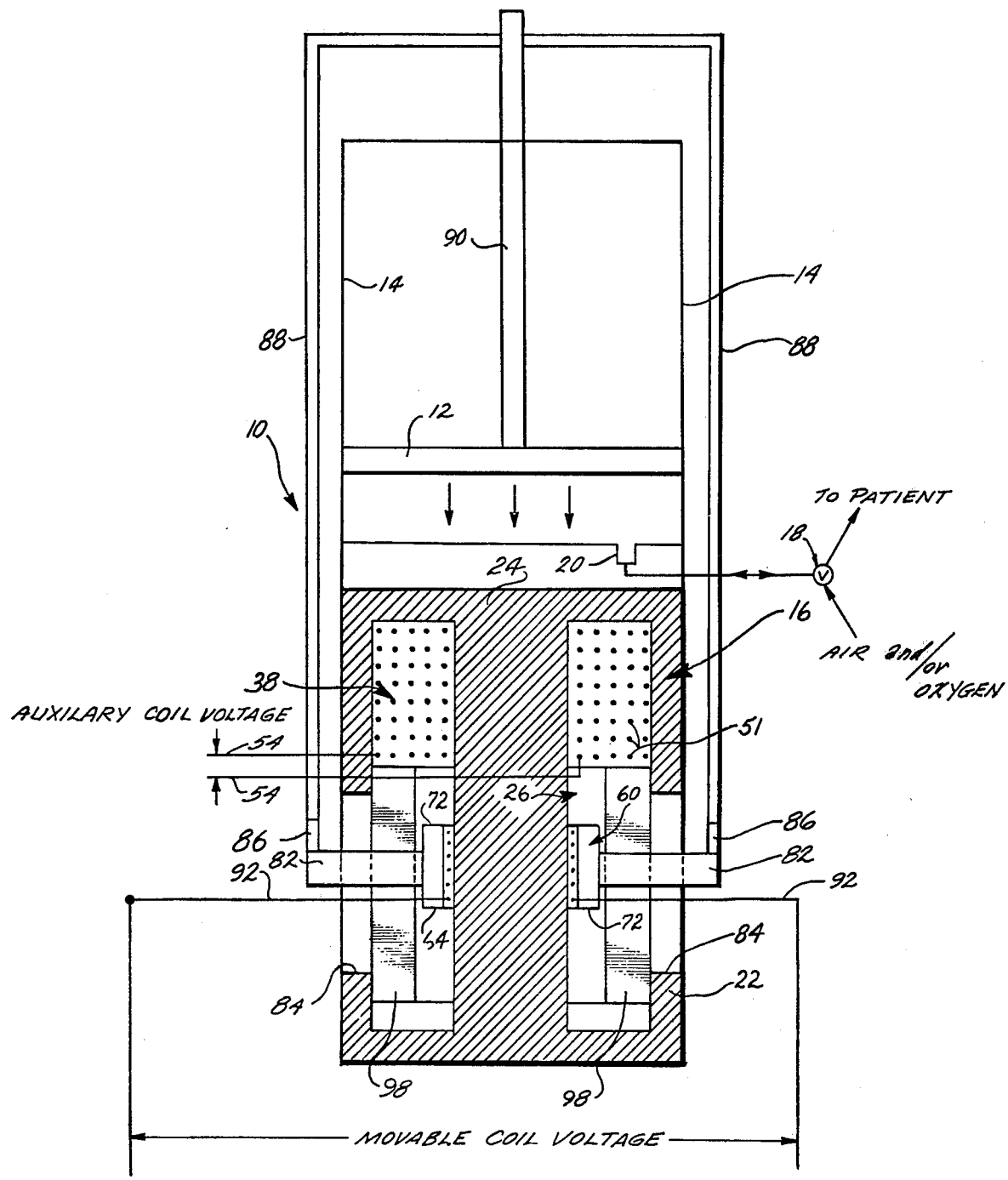
FIG. 1 is a fragmentary schematic elevation view, partly in cross-section, showing a permanent magnet motor in accordance with this invention for driving a piston in a respirator.

Referring to FIG. 1, an air delivery system for a respirator 10 includes a piston 12 disposed in a cylinder 14. The piston is driven vertically back and forth in the cylinder by a permanent magnet motor 16 coupled to the piston by suitable means to be described in detail below.

A supply of gas, usually air, or a suitable mixture of air and oxygen, is delivered to the interior of cylinder 14 through a two-way, solenoid operated valve 18 and port 20. When the permanent magnet motor pulls the piston downward in the direction of the arrows shown in FIG. 1, the gas is forced out through port 20 of cylinder 14, through the valve 18, and through a line (not shown) connected to a patient (not shown) in a conventional manner for delivering the gas to the patient's lungs. The reciprocating movement of the piston periodically pumps the gas into the patient's lungs to replace the inspiratory cycle of normal breathing and allow suitably adjusted time for expiration. The expiratory cycle occurs each time the piston is retracted, with the patient exhaling passively through a separate conduit (not shown) as is well known in the art of respirator therapy. The valve 18 is electrically synchronized with the piston 12. A voltage to the solenoid puts the valve 18 in the inspiratory mode. A synchronizing signal activated in response to movement of the piston turns off the valve solenoid, which moves the valve to connect the patient to atmosphere during the expiratory mode.

The piston moves downward when forcing air into the patient's lungs. This uses the weight of the piston in addition to the force generated by the translational motor to oppose the normal back pressure of the patient's lungs.

Figure 2:
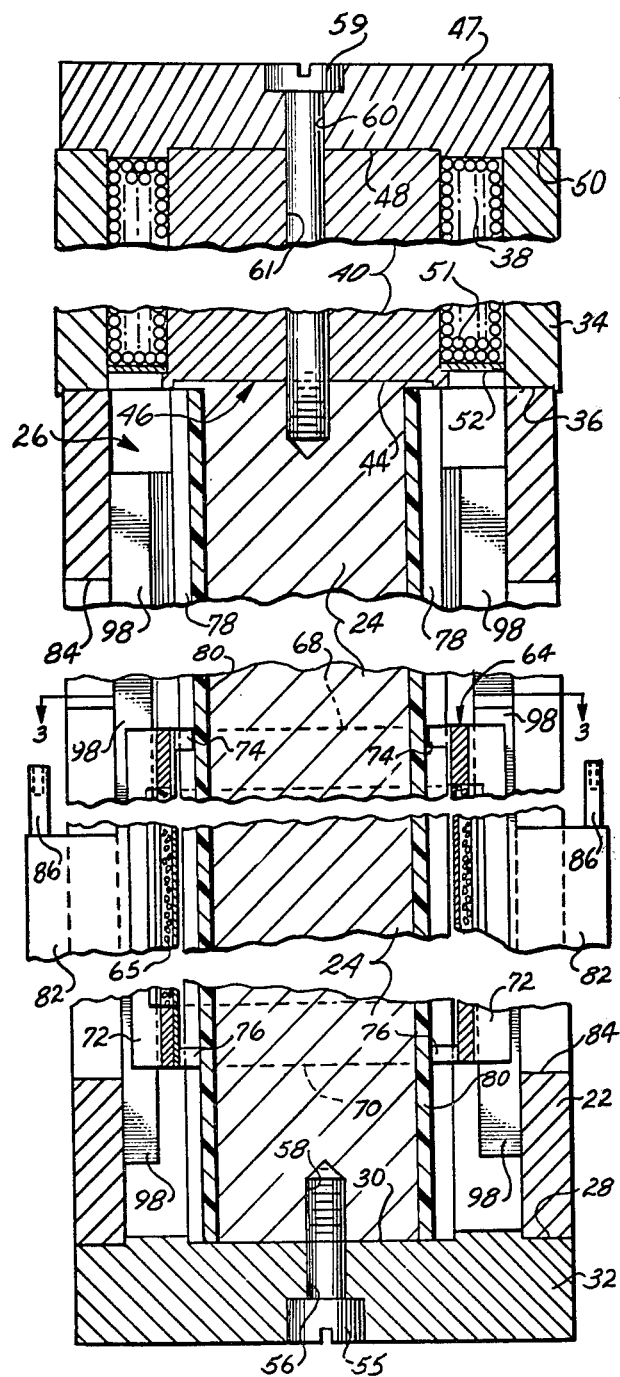
FIG. 2 is a fragmentary cross-sectional elevation view of the permanent magnet motor.
Figure 3:
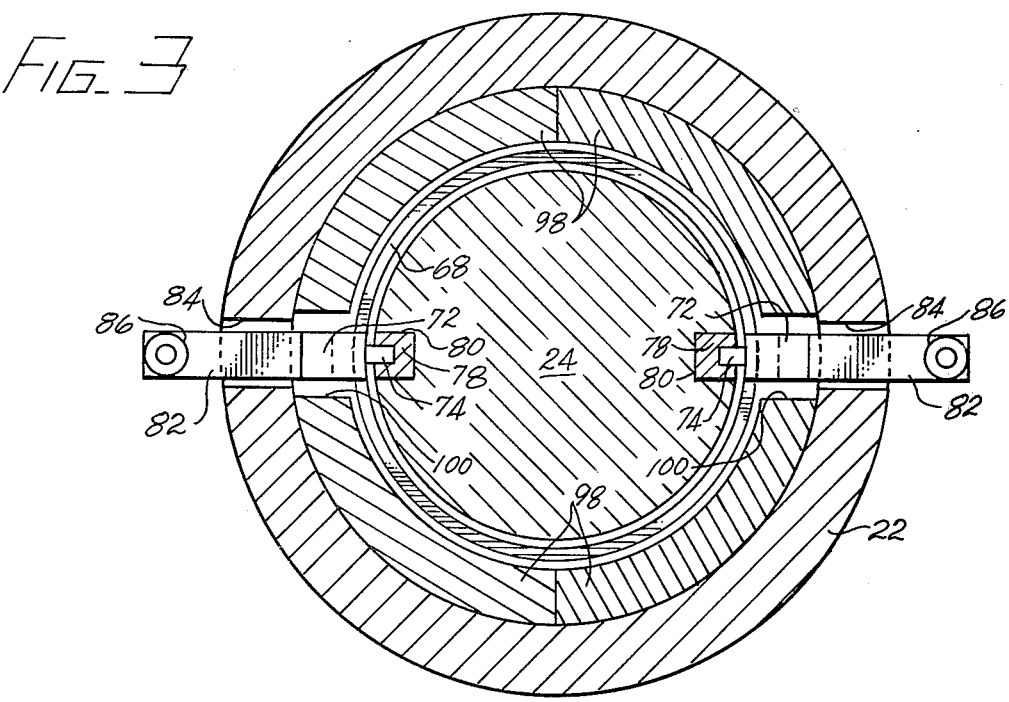
FIG. 3 is a cross-sectional plan elevation view taken on line 3—3 of FIG. 2.

As shown best in FIGS. 2 and 3, permanent magnet motor 16 includes an elongated open-ended cylindrical main shell 22 which is preferably about 14 inches long, with an inside diameter of about 5 inches and a wall thickness of about ⅜ inch.

An elongated solid cylindrical core 24 is disposed centrally within the bore of main shell 22. Core 24 is preferably about 14 inches long, with an outside diameter of about 3½ inches. An annular air gap 26 having a width of about ¾ inch is formed between the outer surface of the core 24 and the inner surface of the main shell 22. Thus, the diameter of the core 24 is more than twice the lateral distance from the O.D. of the core to the O.D. of the wall of main shell 22, the core being of relatively large size so that it can support the magnetic flux developed by the motor.

A stationary auxiliary electromagnet 38 is disposed within the bore of auxiliary shell 34. Electromagnet 38 includes an elongated solid cylindrical auxiliary core 40 having a slightly greater diameter than core 24 and a length almost identical to that of auxiliary shell 34. Auxiliary core 40 contains a circular recess 44 which seats over core 24.

A cylindrical top end plate 47 covers the top of electromagnet 38. Top end plate 47 is the same size as bottom end plate 32. The top ends of auxiliary shell 34 and auxiliary core 40 are seated in circular and annular recesses 48 and 50, respectively, formed in the bottom surface of end plate 47.

An auxiliary coil winding 51 of electromagnet 38 is wound from end to end on core 40 and occupies the approximately ¾ inch wide gap between the core and the interior of auxiliary shell 34. The bottom of winding 51 is supported by an annular plate 52 bonded to the bottom annular surface of the wound coil. Preferably, winding 51 comprises 1075 turns of 18 gauge wire. A pair of leads 54 (see FIG. 1) from winding 51 are connected to a D.C. power supply (not shown) and appropriate circuitry (not shown) to provide proper control described in detail below.

The assembled elements comprising the bottom portion of the permanent magnet motor are joined together by an elongated bolt 55 threaded into matching internally threaded bores 56 and 58 coaxially aligned in bottom plate 32 and the bottom portion of core 24, respectively. The assembled element comprising the top of the motor are joined together by an elongated bolt 59 threaded through a first pair of longitudinally aligned internally threaded bores 60 and 61 extending through end plate 47 and core 40, respectively.

The main structural components of the permanent magnet motor, namely main shell 22, core 24, bottom end plate 32, auxiliary shell 34, auxiliary core 40, and top end plate 47 are made of ferromagnetic materials, preferably steel with a high saturation flux density, to provide the magnetic circuit described in greater detail below.

Figure 4:
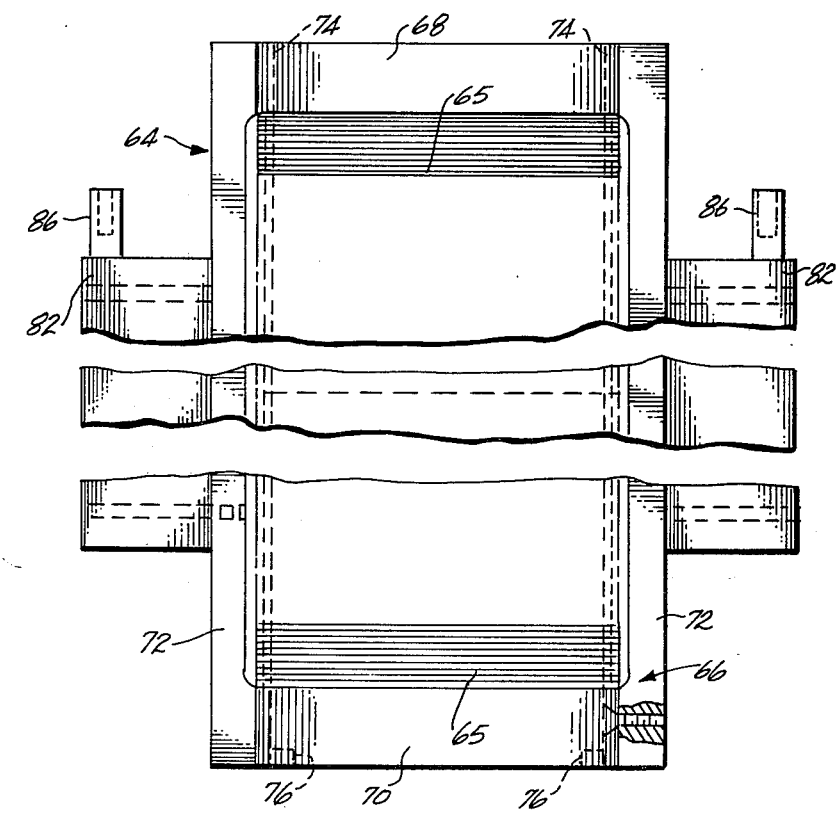
FIG. 4 is a fragmentary elevation view showing a movable coil assembly for the permanent magnet motor.

A movable drive coil assembly 64 (shown in cross-section in FIG. 2 and in elevation in FIGS. 3 and 4) is mounted on core 24 so as to be movable longitudinally relative to the core in the working air gap 26. The movable drive coil assembly includes a pair of relatively thin, elongated, tubular coil elements 65 mounted on one top of the other and surrounding core 24. Coil elements 65 comprise a continuous winding of aluminum ribbon coiled to form an elongated self-supporting ring. Both coil elements 65 together form a movable coil preferably about 6 inches in length from top to bottom. The coils preferably are the type of aluminum ribbon coil used in the Model 14 Head Position System available from Information Magnetics Corporation. The coils are sized so their inside diameter is closely spaced from the outside diameter of core 24, the preferred spacing being about 1/16 inch.

Coils 65 are attached to a carriage 66 comprising a rigid framework formed by a pair of vertically spaced apart, collinear top and bottom rings 68 and 70, respectively, and a pair of opposed vertically extending elongated carriage bars 72 secured to opposite outer edges of the top and bottom rings. Preferably, the top and bottom rings, and their associated carriage bars, are made of aluminum. The top and bottom rings have the same diameter as coils 65, and are held in place tightly against the top and bottom of the coils by the carriage bars. The rings have a narrow longitudinal insulating strip (not shown) to prevent circulating current. The carriage rides vertically back and forth in the air gap 26 when coil assembly 64 moves longitudinally relative to core 24.

The carriage travel is guided by a pair of opposed top ears 74 projecting inwardly from the inner peripheral edge of top rings 68, and a pair of opposed bottom ears 76 projecting inwardly from the inner peripheral edge of bottom ring 70. Both sets of ears are fitted into corresponding longitudinally extending guide channels 78 formed in opposite sides of core 24. Each guide channel includes a U-shaped liner 80 fitted around a corresponding pair of the top and bottom guide ears. Each liner 80 is made of a low-friction material, preferably Teflon.

Corresponding horizontally extending force-distributing ears 82 project outwardly from carriage bars 72. The force-distributing ears extend through corresponding vertically extending elongated slotted openings 84 formed in opposite sides of main shell 22. The force-distributing ears carry corresponding vertically extending mounting pins 86 attached to respective elongated rods 88 (see FIG. 1) which, in turn, are connected to a piston rod 90 for driving piston 12 back and forth in cylinder 14 in response to longitudinally reciprocating travel of movable coil assembly 64.

A pair of flexible lead wires 92 from the winding of coils 65 are connected to a D.C. power supply (not shown) and appropriate control circuitry (not shown) which is separate from the circuitry connected to auxiliary winding 51. Lead wires 92 provide sufficient slack to accommodate movement of coil assembly 64 within air gap 26. The control circuitry will be described in detail below.

Several sets of arcuately curved permanent magnet segments 98 are secured to the inner wall surface of main shell 22 to form the equivalent of an approximately 12-inch long, cylindrically curved, annular permanent magnet surrounding core 24. Preferably, four columns of permanent magnet segments are mounted inside shell 22, each column containing four permanent magnet segments, each segment being approximately three inches long. The permanent magnet segments are secured to each other and to the inner wall of the shell by a suitable bonding material such as epoxy resin. The permanent magnet segments form a continuous annular permanent magnet surrounding the core, except that a pair of narrow, vertically extending spaces 100 are formed 180° apart between the segments along opposite sides of the shell in alignment with slotted openings 84. The two spaces accommodate the carriage bars 72 which ride in respective slotted openings 84 as coil assembly 64 moves relative to core 24. Each permanent magnet segment preferably is about ⅜ inch in thickness, which provides a narrow working air gap of about 3/16 inch between the inner surface of the permannet magnets and the outer surface of core 24 for accommodating coil elements 65 of the movable coil assembly. This air gap is as narrow as possible to minimize the leakage flux generated by the permanent magnet which, in turn, increases the force and stroke length of the motor.

The annular permanent magnet develops a radial magnetic field across working air gap 26. When the lead windings of the movable coil are connected to the control circuitry, a tangential current flows through the moving coil. This current interacts with the radial magnetic field to produce a translational force on the movable coil assembly parallel to the longitudinal axis of core 24. The force developed by the movable coil is uniformly brought out of the motor by the opposed force-distributing ears 82 which transmit the force, through rods 88, to the respirator piston. Since the coil and the respirator move as a unit in a vertical direction, the magnetic fluid generated by the permanent magnet motor is symmetrical around the drive coil and therefore automatically self-centers the drive coil and piston. This eliminates the need for additional mechanical linkages which would be otherwise needed to overcome the force of gravity if the coil and piston are mounted horizontally.

The respirator of this invention is capable of delivering two liters of air at a maximum pressure of 100 cm. $H_2O$. The relatively long stroke (about 6 to 10 inches) of motor 10 insures delivery of the desired two liter volume of air. A motor output force of about 42 pounds will produce the desired 100 cm. $H_2O$ maximum pressure. Generally speaking, an output force up to about 36 pounds will produce the pressures necessary for most patients needing respirator therapy.

The flux density of the permanent magnet segments, together with the size of core 24 and the size of air gap 26, are critical in enabling the motor to produce the relatively long stroke and an output force up to approximately 36 pounds without use of the auxiliary winding. The permanent magnet segments are made of a ferrite M-7 material manufactured by Allen Bradley Co., with a flux density of 3400 gauss and a coercive force of 3250 oersteds. Steel core 24 has a cross-sectional area of approximately 9 square inches and a length of about 14 inches, which provide a sufficient cross-sectional area of ferromagnetic material to support the flux required to generate the relatively large force necessary for the respirator without driving the core into saturation. The relatively high flux density of the annular permanent magnet, together with the relatively narrow (3/16 inch) working air gap between the permanent magnet segments and core 24, combine to produce the large magnetic flux required for the respirator drive. (The narrow air gap prevents most of the flux generated by the permanent magnets from being dissipated). The relatively narrow wall thickness of the aluminum coil elements 65 allows such a narrow air gap to be used. (If the movable coil is a continuous winding of conventional insulated conductor wire, the air gap would have to be widened to accommodate the coil, and a wider air gap would reduce the effective flux available to obtain the large output force.)

The flux path of the main permanent magnet field is radially across air gap 26, symmetrically in both directions through core 24 toward the ends of the core, radially across both end plates 32, 47, and in the walls of main shell 22 and auxiliary shell 34. The combined wall thickness of the main outer shell, auxiliary shell, and end plates provides an area of ferromagnetic material at least equal to the area of core 24, and therefore is sufficient to support the flux carried in core 24.

The two closed ends of the motor shell concentrate the magnetic lines of flux to the area within the shell, which enables the relatively long stroke length to be obtained. When compared with a motor having one closed end, the present motor reduces substantially the number of permanent magnets required, and the volume of ferromagnetic material necessary to produce the desired force and stroke length.

The permanent magnet translational motor 10 has a sufficiently long stroke length and develops a sufficiently high force to provide the necessary volume of air at the pressures required for respirator therapy, whether it be for normal partients, or those with high airway resistance or compliance problems. Moreover, the translational motor provides a simple means for controlling movement of the respirator piston to deliver a controlled time-related volume of gas to a patient throughout each inspiratory cycle. A D.C. voltage is applied to the drive coil to generate an electrical current in the coil winding. The drive coil control circuitry has the capability of varying the amount of current in the drive coil. Generally speaking, the amount of current in the drive coil is directly proportional to the output force of the motor. Therefore, an increase in the current level in the coil increases the force applied to the piston. An adjustable D.C. voltage waveform is applied to the drive coil to control the pressure build up in the patient's lungs with respect to time during each inspiratory cycle of the respirator. For instance, if patient airway resistance increases, the current in the coil can be adjusted to keep the piston from slowing down in response to the increased load. The control circuitry also allows the force developed by the respirator piston to be set at different levels depending upon the desired pressure build up in each patient's lungs. The circuitry also provides a simple means for controlling the frequency of the inspiratory cycles by controlling the rate of the piston to produce desired breathing rates, say from 3 to 60 bpm. Moreover, the current in the drive coil is reversible so that the piston can be positively driven backwards as well as forwards.

Preferably, the O.D. of the piston 12 is coated with a thin layer of low friction, self-lubricating material such as Teflon. The Teflon is baked on to the O.D. of the piston at high temperatures, say about 600° F. The Teflon coating is then machined down to a thickness of about 2 mils.

The I.D. of the cylinder 14 has a layer of nickel plate applied, preferably by electro-deposition techniques, to obtain a uniform layer of about $\frac{1}{2}$ mil thick. The Teflon is machined to exactly fit into the I.D. of the nickel plated cylinder. A clearance of less than about 0.5 mil is provided between the piston and cylinder. This construction eliminates O-ring seals, or the like, and during use is highly effective in holding the large pressures necessary for respirator therapy with substantially no leakage. This construction also eliminates the need for hydrocarbon lubricants which can be a hazard when operating in 100 percent oxygen atmospheres, and also insures the purity of air being fed to the patient. The main bodies of the piston 12 and cylinder 14 are made from aluminum so that the coefficient of expansion of the piston and cylinder will be the same.

Auxiliary electromagnet 38 varies the maximum output force developed by the motor. Electric current flowing through the auxiliary coil winding provides additional magnetomotive force which controls the magnetic saturation in auxiliary core 40 and top of core 24. The direction and magnitude of the current flow in the auxiliary winding can be adjusted to effectively add flux to take core 40 out of saturation. This additional flux accommodates greater current flow in the moving coil, and in effect adds to the output force developed by the motor.

The graph shown in FIG. 5 illustrates how the current in the axuiliary winding can vary the output force of the motor over a relatively wide range. The motor develops an output force of 36 pounds when there is no current flow in the auxiliary winding. As discussed above, this force allows the respirator to provide the desired two liter volume of gas at pressures necessary for most patients needing respirator therapy. The graph of FIG. 5 shows that the current in the auxiliary coil can be increased to the point where the motor produces a maximum force of about 46 pounds. This output force provides two liters of gas at a pressure of more than 100 cm. $H_2O$, which easily meets the requirements of patients under respirator therapy.

The permanent magnet motor by its nature provides a simple means for controlling movement of the piston to deliver a controlled, time-related volume of gas to the patient throughout each inspiratory cycle. The purpose of the desired time-dependent adjustment of the piston movement is to provide the capability of controlling the pressure build up in the patient's lungs during each inspiratory cycle to prevent excessive pressure build up which, in turn, could cause injury to the patient's lungs. The auxiliary electromagnet allows the maximum force available from the motor to be electronically controlled. The instantaneous pressure build up in the patient's lungs during each inspiratory cycle can be monitored, and the desired time-dependent pressure within the patient's lungs can be controlled by external circuitry (not shown) which alters the current flow through the auxiliary coil. This provides an immediate adjustment in the force developed by the respirator, and the force, in turn, controls the instantaneous pressure build up in the patient's lungs.

The use of the auxiliary coil also produces a larger output force than would be possible if additional permanent magnets alone were used to gain the additional output force. Additional permanent magnets alone would not produce an increase in output force unless the cross-sectional areas of core 24 and shell 22 were increased sufficiently to accommodate the additional flux. The auxiliary coil provides a cost savings in material when compared with the cost of additional permanent magnets and material for the core and outer shell.

The permanent magnet motor described herein is especially advantageous when used as the drive for a respirator piston because the respirator has no moving parts, other than the piston itself and the movable drive coil assembly. No racks, joints, pinions, gear reduction, or other similar movable parts used in conventional respirators are necessary. The result is a respirator of extreme mechanical simplicity, reliability and accurate control. Moreover, this motor is essentially silent during operation, which is a substantial improvement over the noisy rotary type motors commonly used in respirators.

We claim:

1. An air delivery system for a respirator capable of applying at least 36 pounds of force to a respirator piston through a stroke length of at least six inches, the air delivery system comprising
    (a) a cylinder and a piston movable in the cylinder for forcing air to a patient through an air outlet in the cylinder,
    (b) a translational motor for moving the piston which includes a shell adjacent the cylinder and having an outer wall with a pair of closed ends forming an enclosed hollow interior of the shell,
    (c) an elongated core extending through the hollow interior of the shell between the closed ends thereof,
    (d) permanent magnet means in the hollow interior surrounding a predetermined length of the core, the permanent magnet means being spaced from the core to form a narrow working air gap surrounding the core and extending laterally from the outer surface of the core to the permanent magnet means, whereby a magnetic field is established across the narrow working air gap,
    (e) a movable drive coil surrounding the portion of the core located in the working air gap, the drive coil being movable along the length of the core in the magnetic field in response to changes in electric current passing through the drive coil, the working air gap being substantially void between the outer surface of the core and the permanent magnet means so as to be as narrow as possible but still accommodate the movable drive coil, and
    (f) drive means extending outwardly from the drive coil through corresponding openings in the shell outer wall and connecting the piston to the drive coil to apply reciprocating translational motion to the piston in response to movement of the drive coil.

2. An air delivery system according to claim 1 including longitudinally extending, elongated grooves formed in opposite sides of the core, and in which the drive coil includes cooperating shoulders slidably disposed in the grooves for guiding movement of the coil along the length of the core.

3. An air delivery system according to claim 1 in which the openings in the shell outer wall are spaced 180° apart, and in which the permanent magnet means are annular and surrounds substantially the entire portion of the core and the working air gap except along the openings in the shell outer wall.

4. An air delivery system according to claim 3 including opposed mounting means spaced 180° apart, and extending radially outwardly through the openings in the shell outer wall, and a pair of longitudinally extending opposed carrier bars secured to the mounting members and extending to the piston to provide means for longitudinally reciprocating the piston in response to movement of the drive coil.

5. An air delivery system according to claim 1 in which the O.D. of the core is at least about two times the lateral distance from the O.D. of the core to the O.D. of the shell outer wall.

6. An air delivery system according to claim 1 in which the O.D. of the piston has a coating of a low-friction, self-lubricating material and is closely fitted into the I.D. of the cylinder for sliding movement therein independently of the use of lubricants or O-ring seals.

7. An air delivery system according to claim 6 in which the O.D. of the piston is coated with a layer of Teflon.

8. In an air delivery system for a respirator which includes a cylinder and a piston movable in the cylinder for forcing air to a patient through an air outlet in the cylinder, improved means for applying at least 36 pounds of force to the piston through a stroke length of at least six inches, the improvement comprising a permanent magnet translational motor which includes:
    (a) a closed ferro-magnetic shell having an outer wall with a pair of closed ends forming an enclosed hollow interior of the shell,
    (b) an elongated ferro-magnetic core extending through the hollow interior of the shell from one closed end to the other, the shell having an inner surface spaced from an outer surface of the core,
    (c) permanent magnet means secured to the inner surface of the shell, the permanent magnet means surrounding a predetermined length of the core and being spaced from the core substantially around the entire outer surface of the core along said predetermined length to form a narrow elongated working air gap between the core and the permanent magnet means whereby a magnetic field is established across the working air gap,
    (d) a movable drive coil surrounding the portion of the core located in the working air gap, the working air gap being substantially void between the outer surface of the core and the permanent magnet means so as to be as narrow as possible but still allow passage of the movable drive coil, the drive coil being reciprocally movable along the length of the core in the magnetic field in response to changes in electrical current passing through the drive coil, (e) drive means extending outwardly from the drive coil through corresponding elongated openings in the shell outer wall for connecting the drive coil to the respirator piston to apply reciprocating translational motion to the piston at said force over said stroke length in response to corresponding movement of the drive coil, and (f) a cooperating shoulder and groove means between the drive coil and the outer surface of the core for providing guided translational movement of the drive coil along the core.

9. An air delivery system according to claim 8 in which the diameter of the core is at least twice as wide as the radial distance from the outer surface of the core to the outside surface of the shell outer wall.

10. In an air delivery system for a respirator which includes a cylinder and a piston movable in the cylinder for forcing air to a patient through an air outlet in the cylinder, improved means for applying at least 36 pounds of force to the piston through a stroke length of at least six inches, the improvement comprising a permanent magnet translational motor which includes:

(a) a closed ferro-magnetic shell having an outer wall with a pair of closed ends forming an enclosed hollow interior of the shell, (b) an elongated ferro-magnetic core extending through the hollow interior of the shell from one closed end to the other, the shell having an inner surface spaced from an outer surface of the core, (c) permanent magnet means secured to the inner surface of the shell, the permanent magnet means surrounding a predetermined length of the core and being spaced from the core around substantially the entire outer surface of the core along said predetermined length to form an elongated, narrow working air gap between the core and the permanent mgnet means whereby a magnetic field is established across the working air gap, (d) a movable drive coil surrounding the portion of the core located in the working air gap, the working air gap being substantially void between the outer surface of the core and the permanent magnet means so as to be as narrow as possible but still allow passage of the movable drive coil, the drive coil being reciprocally movable along the length of the core in the magnetic field in response to changes in electric current passing through the drive coil, and (e) drive means for extending from the drive coil to the respirator piston to apply reciprocating translational motion to the piston at said force over said stroke length in response to corresponding movement of the drive coil.

11. The improvement according to claim 10 in which the working air gap is no more than about 3/16 inch wide.

12. The improvement according to claim 10 in which the diameter of the core is at least twice as wide as the radial distance from the outer surface of the core to the outer surface of the shell outer wall.

13. The improvement according to claim 12 in which the working air gap is no more than about 3/16 inch wide.

* * * * *